(12) United States Patent
Balestracci (10) Patent No.: US 6,240,788 B1
(45) Date of Patent: Jun. 5, 2001

(54) METHOD AND APPARATUS FOR MEASUREMENT OF BREAKAWAY AND RUNNING FORCES OF A PLUNGER IN A SYRINGE BARREL

(75) Inventor: Ernest Balestracci, Iselin, NJ (US)

(73) Assignee: Bracco Diagnostics, Inc., Princeton, NJ (US)

( * ) Notice: Subject to any disclaimer, the term of this patent is extended or adjusted under 35 U.S.C. 154(b) by 0 days.

(21) Appl. No.: 09/504,100

(22) Filed: Feb. 15, 2000

Related U.S. Application Data (62) Division of application No. 09/259,748, filed on Feb. 27, 1999, now Pat. No. 6,105,230.

(51) Int. Cl.[7] .................. G01L 5/00; G01N 3/02
(52) U.S. Cl. .......................... 73/862.01; 73/856
(58) Field of Search ............... 29/407.01, 407.05, 29/407.08, 235, 239, 256, 266, 426.5, 407.1; 604/65, 66, 67, 31; 73/862.01, 831, 856

(56) References Cited

U.S. PATENT DOCUMENTS

| | | | |
|---|---|---|---|
| 4,068,798 | 1/1978 | Rohde | 233/26 |
| 4,435,173 * | 3/1984 | Siposs et al. | 604/155 |
| 4,522,089 | 6/1985 | Alvi | 81/3.42 |
| 4,563,175 * | 1/1986 | LaFond | 604/155 |
| 4,753,115 * | 6/1988 | Moody | 73/862.01 |
| 4,838,857 * | 6/1989 | Strowe et al. | 604/67 |
| 4,876,926 | 10/1989 | Muszak | 81/3.2 |
| 4,908,017 * | 3/1990 | Howson et al. | 604/67 |
| 4,919,134 * | 4/1990 | Streeter | 128/400 |
| 4,952,205 * | 8/1990 | Maurerer et al. | 604/67 |
| 4,982,553 | 1/1991 | Itoh | 53/246 |
| 5,139,484 * | 8/1992 | Hazon et al. | 604/155 |
| 5,244,461 * | 9/1993 | Derlien | 604/65 |
| 5,354,273 * | 10/1994 | Hagen | 604/66 |
| 5,490,321 | 2/1996 | Kaneko | 29/714 |
| 5,798,467 * | 8/1998 | Hasegawa et al. | 73/862.01 |
| 5,819,508 | 10/1998 | Kraft et al. | 53/492 |
| 6,067,696 * | 5/2000 | Cecil et al. | 29/407.01 |
| 6,104,896 * | 8/2000 | Zaman et al. | 29/407.08 |

FOREIGN PATENT DOCUMENTS

WO 97/03915    2/1997    (WO).

* cited by examiner

*Primary Examiner*—S. Thomas Hughes
*Assistant Examiner*—Marc Jimenez
(74) *Attorney, Agent, or Firm*—Imre Balogh (57) ABSTRACT

Method and apparatus for measuring the breakaway and running forces required to move the plunger from its initial position toward the distal end of the syringe or cartridge barrel.

2 Claims, 8 Drawing Sheets

METHOD AND APPARATUS FOR MEASUREMENT OF BREAKAWAY AND RUNNING FORCES OF A PLUNGER IN A SYRINGE BARREL

CROSS REFERENCE TO RELATED APPLICATIONS

This is a divisional of application Ser. No. 09/259,748, filed Feb. 27, 1999, now U.S. Pat. No. 6,105,230.

BACKGROUND OF THE INVENTION

1. Field of the Invention

This invention relates to a method and apparatus for removing an elastomeric closure from a pre-filled syringe barrel, measuring the force required to remove the elastomeric closure from the pre-filled syringe barrel, and then measuring the breakaway and running forces required to move the plunger in the pre-filled syringe barrel from its proximal position toward the distal end of the barrel.

2. Reported Developments

Pre-filled syringe barrels or cartridges without an access means, such as a needle, contain injectable solutions therein. The syringe barrels or cartridges are stoppered by elastomeric closures, such as soft rubber stopper-like devices, at the distal, tapered end thereof, while the proximal end of the barrels are closed by slidable plungers. Prior to use a plunger rod is inserted into the plunger so that manual pressure can be exerted on the plunger for dispensing the injectable fluid from the barrel. The syringe barrels or cartridges are autoclaved or sterilized by other means and packaged ready for use.

The elastomeric closure in the form of a soft rubber stopper comprises a wall across the mouth opening of the tapered barrel and a plug depending therefrom which is inserted into the mouth opening of the barrel. The elastomeric closure allows easy insertion into the barrel to form a tight seal therewith and is designed to maintain the integrity of the seal during autoclaving. Removal of the elastomeric closure is often required prior to use of the injectable solution, such as for verifying that the elastomeric closure remains in place during storage and will not accidentally be removed, for testing the integrity of the injectable solution, or for measuring the breakaway and running forces necessary to move the plunger from its initial position at the proximal end of the barrel toward the distal end of the barrel. On extended shelf-life the elastomeric closure tends to develop a strong physical bond with the wall of the barrel making manual removal cumbersome. The removal of an elastomeric stopper from a glass syringe barrel carries the risk of injury to the operator since the glass may shatter when held manually.

The prior art provides for removal of closures from tubes and vials containing biological and other samples therein. The removal of such closures is often accomplished with automated sample handling systems designed to handle large number of tubes and vials. Illustrative examples of such systems are disclosed in the following references.

U.S. Pat. No. 4,068,798 discloses a method for stopper removal comprising the steps of: suspending a test tube by its stopper; and subjecting the suspended test tube to a centrifugal force to cause the tube to separate from the stopper under the influence of the centrifugal force.

U.S. Pat. No. 4,982,553 discloses an automatic apparatus for pulling out test tube stoppers. The apparatus includes a plug extracting mechanism comprising a U-shaped stationary frame having tube-clamping members to hold a tube therein; and plug-extracting cylinders having styluses which pierce the plug contained in the tube to extract the plug.

U.S. Pat. No. 5,490,321 discloses a method and apparatus for removing a stopper from a container, the apparatus comprising a container holder and claw members. The claw members are driven by a linear drive source and a swinging motion drive source. The stopper is removed from the material holding container while applying a pull-up force and twist force to the fitted stopper.

U.S. Pat. No. 4,876,926 discloses a stopper-removal apparatus which comprises: a first mechanism for gripping the container against rotation; a second mechanism for gripping the stopper; and a drive for rotating the second mechanism about an axis while the second mechanism grips the stopper. The stopper removal apparatus includes an annular ring having a plurality of small spikes non-radially aligned which grip the stopper only if the ring is rotated in one direction, and slip off the stopper when the rotating drive rotates in a direction opposite to the one direction.

It is an object of the present invention to provide a method and an apparatus for removing elastomeric closures from pre-filled syringe and cartridge barrels and to measure the force required for their removal.

It is another object of the present invention to determine the force necessary to initially move the plunger in the barrel referred to as breakaway force, and to determine the force necessary to continue movement of the plunger, variously referred to as push, gliding or running force, while maintaining the required output from the barrel.

SUMMARY OF THE INVENTION

In one aspect the present invention provides a method and apparatus for removing an elastomeric closure or tip from a pre-filled barrel of a syringe or cartridge and measuring the force required for the removal.

In another aspect the present invention provides a method and an apparatus for measuring the breakaway and running forces required to move the plunger from its initial position at the proximal end of a pre-filled barrel and to maintain the movement of the plunger toward the distal end of the barrel to expel the content of the barrel.

The apparatus for removing the elastomeric closure comprises: a housing of generally rectangular box-shape configuration having a horizontal bottom portion, a horizontal top portion and vertical side portions connected to the top and bottom portions enclosing a rectangular shape space therebetween; an electronically movable horizontal member positioned parallel to and adjacent the horizontal top portion extending to the vertical side portions, wherein said movable member is adapted to travel vertically between said horizontal top and bottom portions;

electronic drive and force measuring means for moving the movable member;

a barrel mounting means affixed to the bottom portion of the housing for holding the barrel by its flange in an upright position, said barrel being equipped with the elastomeric closure; and a threaded rod having a distal end and a proximal end, attached to the movable member at the distal end thereof, and the proximal end is attached to a locking bar to grip said elastomeric closure and remove the closure from the barrel when the movable member is electronically moved toward the horizontal top portion of the housing.

The apparatus for measuring the breakaway and running forces required to move a plunger from its initial position at the proximal end of a barrel and to maintain the movement of the plunger toward the distal end of the barrel to expel the content thereof, said barrel containing an injectable solution therein and from which the elastomeric closure is removed, comprises:

a housing of generally rectangular box-shape configuration having a horizontal bottom portion, a horizontal top portion and vertical side portions connected to the top and bottom portions enclosing a rectangular shape space therebetween, and electronically movable horizontal member positioned parallel to and adjacent the horizontal top portion extending to the vertical side portions, wherein said movable member is adapted to travel vertically between said horizontal top and bottom portions, electronic drive and measuring means for moving the movable member and for measuring the breakaway and running forces;

a barrel mounting block having a distal end, a proximal end and cylindrical side portions enclosing a cylindrical cavity therein to receive and hold a barrel in an upside down position therein, said barrel mounting block is positioned on the horizontal bottom portion of the housing;

a rod having a distal end and a proximal end attached by its distal end to the movable member, and the proximal end having means to engage and grip the plunger positioned at the proximal end of the barrel to move the plunger from its stationary position toward the distal end of the barrel whereby said electronic drive and measuring means measures the breakaway and running forces required to start moving said plunger in said barrel, and to maintain the movement of said plunger to expel its content.

The invention further provides a method for removing an elastomeric stopper from the barrel of a syringe or cartridge and measuring the force of removal, and for measuring the breakaway and running forces required to move the plunger from its initial position at the proximal end of the barrel toward the distal end of the barrel and to maintain the movement of said plunger toward the distal end of the barrel.

The method of removing an elastomeric stopper from the barrel of a syringe or cartridge and for measuring the removal force required to remove the elastomeric stopper from the barrel comprises the steps of:

holding the barrel in a stationary position;

engaging the elastomeric stopper with a gripping means which is attached to a vertically moveable member; and moving said movable member by electronic means relative to said stationary barrel whereby the elastomeric closure is separated from said barrel, and measuring the removal force by measuring means.

The method of measuring the breakaway and running forces required to move a plunger from its initial position in the proximal end of the barrel and maintaining the movement of the plunger toward the distal end of the barrel, said barrel containing an injectable solution therein and from which the elastomeric stopper is removed, comprises the steps of positioning the barrel in a barrel mounting block having a cylindrical cavity therein in an upside down position for holding the barrel in an upside down position;

releasably connecting the proximal end of the plunger to a vertically movable member;

moving the plunger from its stationary position toward the distal end of the barrel by electronic drive means; and measuring the breakaway and running forces required to move said plunger in said barrel by electronic measuring means.

DETAILED DESCRIPTION OF THE INVENTION

Figure 1:
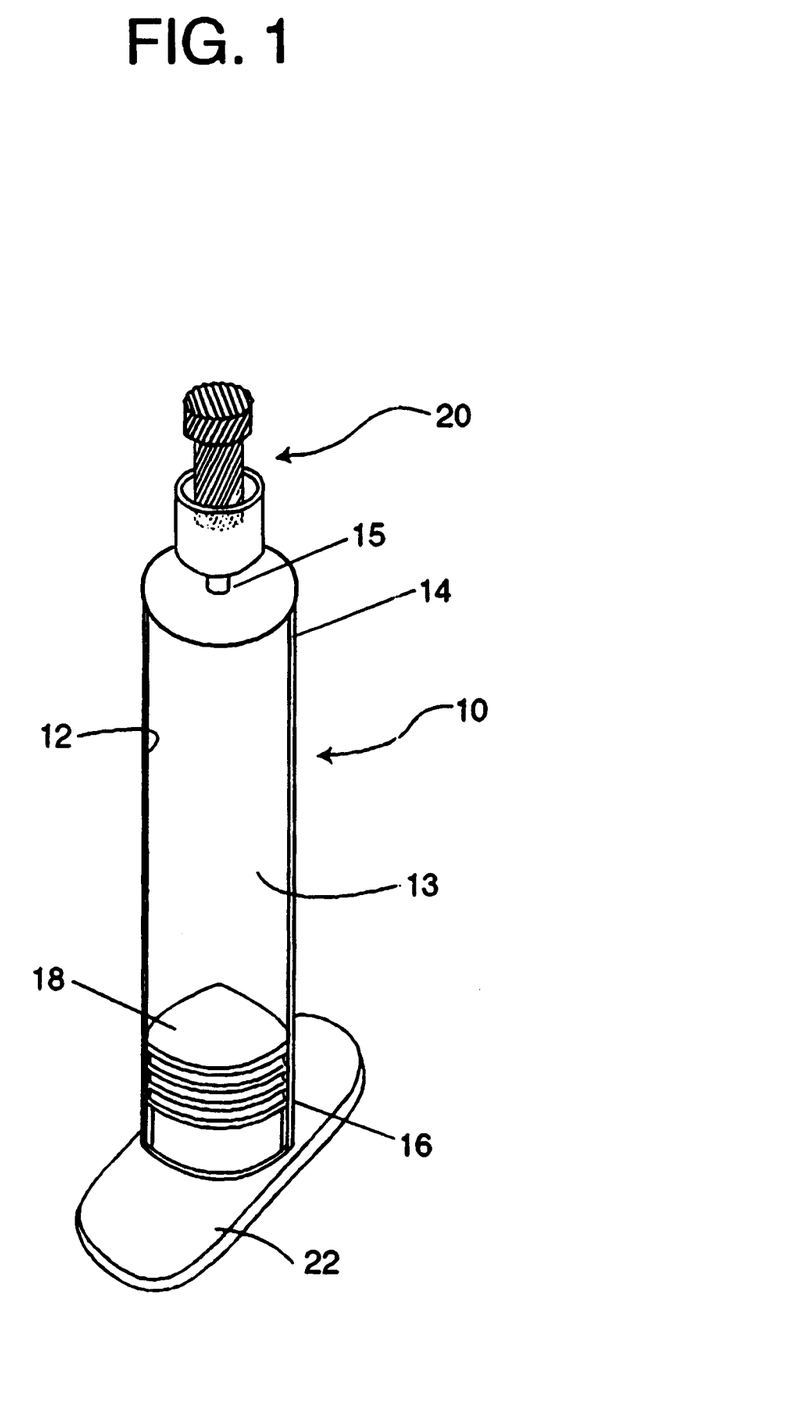
FIG. 1 shows in a perspective view a typical cartridge barrel filled with an injectable solution stoppered by an elastomeric closure at the end thereof and stoppered by a plunger at the proximal end thereof.

FIG. 1 shows a typical cartridge or syringe barrel 10 of glass or polymeric material having an inner surface 12 defining a cylindrical chamber 13 for retaining a fluid therein. The barrel has a distal end 14 terminating in a tapered tip 15 having a bore therethrough to which an injection needle or a connector with a tubing conduit can be attached and a proximal end 16 for receiving a plunger 18 which retains the fluid and which, upon use, expels the fluid from the barrel when an external pressure is exerted thereon. The tapered end having the bore therein is stoppered by an elastomeric closure 20, such as a soft rubber stopper for hermetically sealing the distal end of the barrel. At its proximal end the plunger is equipped with a flange 22 to facilitate handling the barrel. When the fluid is an injectable solution, the barrel along with its content is sterilized, preferably by autoclave. After sterilization the cartridge barrel is packaged and stored ready for used when needed.

During shelf life the content of the barrel is checked at certain time intervals to ascertain that the content is within the prescribed range of the properties necessary for safety and efficacy and for measuring the removal force to ascertain that the elastomeric closure is tightly sealing the barrel. When testing the content of the barrel the elastomeric closure is removed to expel a certain amount of the content. At extended shelf life of the solution it was found that the elastomeric closure is difficult to remove manually.

The cartridge or syringe barrel containing an injectable fluid therein is also tested for the force necessary to start the plunger moving in the distal direction and to move the plunger smoothly toward the distal end of the barrel in expelling the injectable fluids from the barrel. These forces are commonly referred to as breakaway forces and running or guiding forces respectively.

Figure 2:
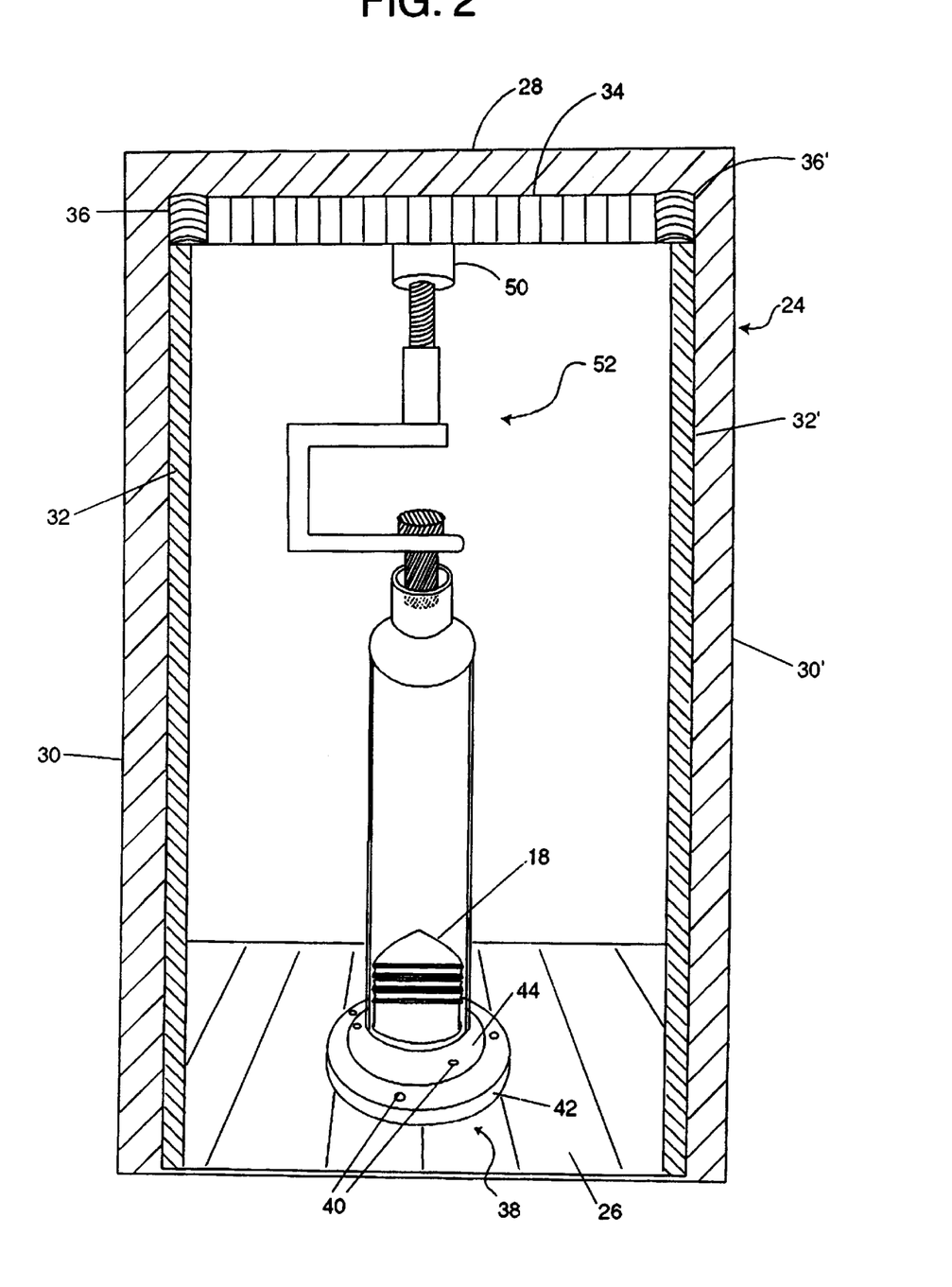
FIG. 2 shows in a perspective view the apparatus for removing an elastomeric closure, the apparatus containing the cartridge barrel shown in FIG. 1.

FIG. 2 shows in perspective view the apparatus of the present invention for removing the elastomeric closure. The apparatus includes a housing 24 of a generally rectangular box-shape configuration having a horizontal bottom portion 26 which serves as a platform, a horizontal top portion 28, and vertical side portions 30 and 30' connected to the top and bottom portions enclosing a rectangular space therebetween in which the remaining portions of the apparatus are located. Adjacent and parallel to vertical side portions 30 and 30' are male-threaded guidance rods 32 and 32' affixed to vertical side portions 30 and 30'. Horizontal member 34 extending to threaded guidance rods 32 and 32' are equipped at its end portions 36 and 36' with female threaded means for slideable vertical movement on the threaded guidance rods. Horizontal member 34 is designed to travel vertically between said horizontal top portion and said horizontal bottom portion. Electronic drive and control means (not shown) move the horizontal member vertically which control means can be equipped with electronic data output means expressing the force required to move the horizontal member and testing feature removably attached to it. Such equipment is well known in the prior art and is available from Instron Corporation, MA, for example INSTRON Series 5500.

Figure 3:
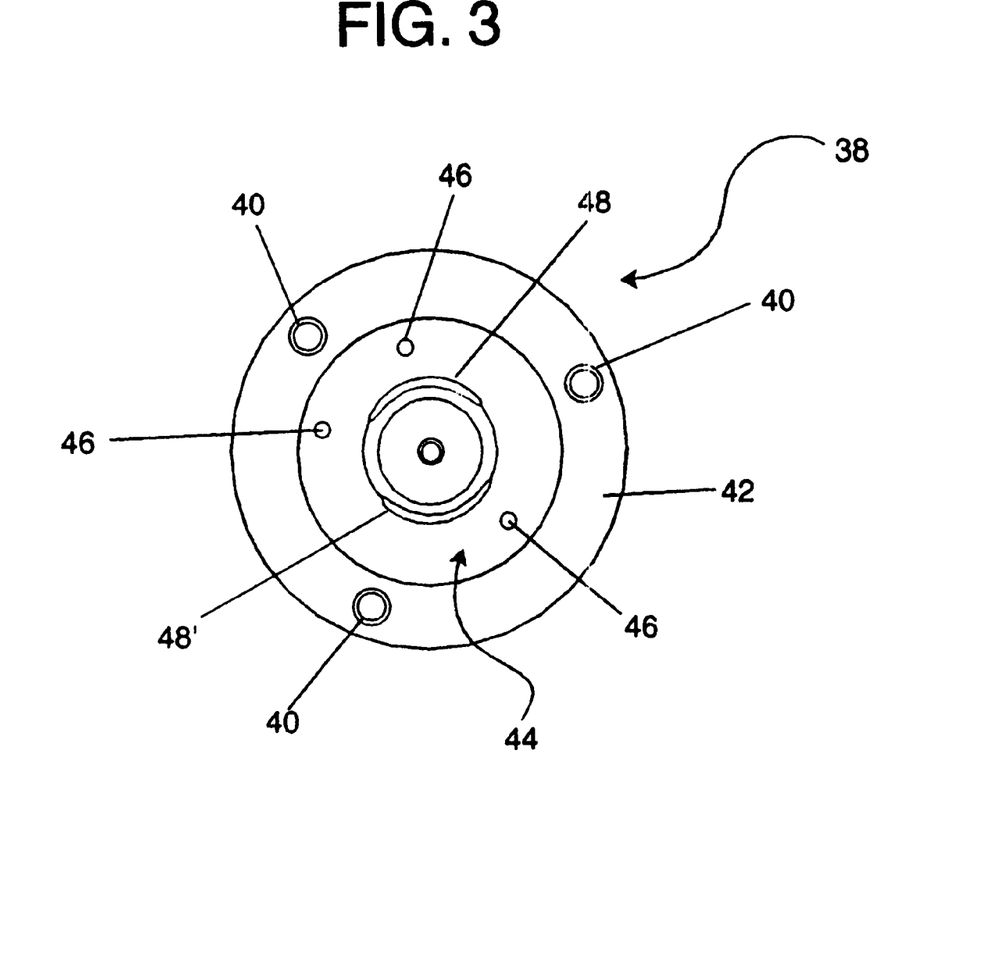
FIG. 3 shows in a top plan view a mounting plate and clamp ring which hold the cartridge barrel in position in the apparatus shown in FIG. 2.
Figure 4:
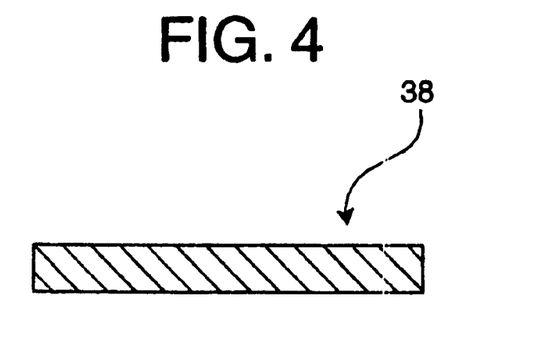
FIG. 4 shows a side elevational view of the mounting plate and clamp ring of FIG. 3.

Barrel mounting means 38 is affixed and is fastened to the bottom portion of housing 26 by bolts 40 and comprises: a mounting plate 42 and clamp ring 44. Clamp ring 44 is attached to mounting plate 42 as shown in FIG. 2 in perspective view and in top plan view in FIG. 3 and side elevational view in FIG. 4. Barrel mounting means holds a barrel of a syringe or cartridge in place in an upright position when the elastomeric closure is being removed from the tip of the barrel. Clamp ring 44 is attached to mounting plate 42 by bolts 46. Clamp ring 44 comprises slots 48 and 48' designed to receive and engage flange 22 of barrel 10 shown in FIG. 1.

Horizontal member 34 is equipped at about its center portion with a rod receiving member 50 having internal threads therein.

Figure 5:
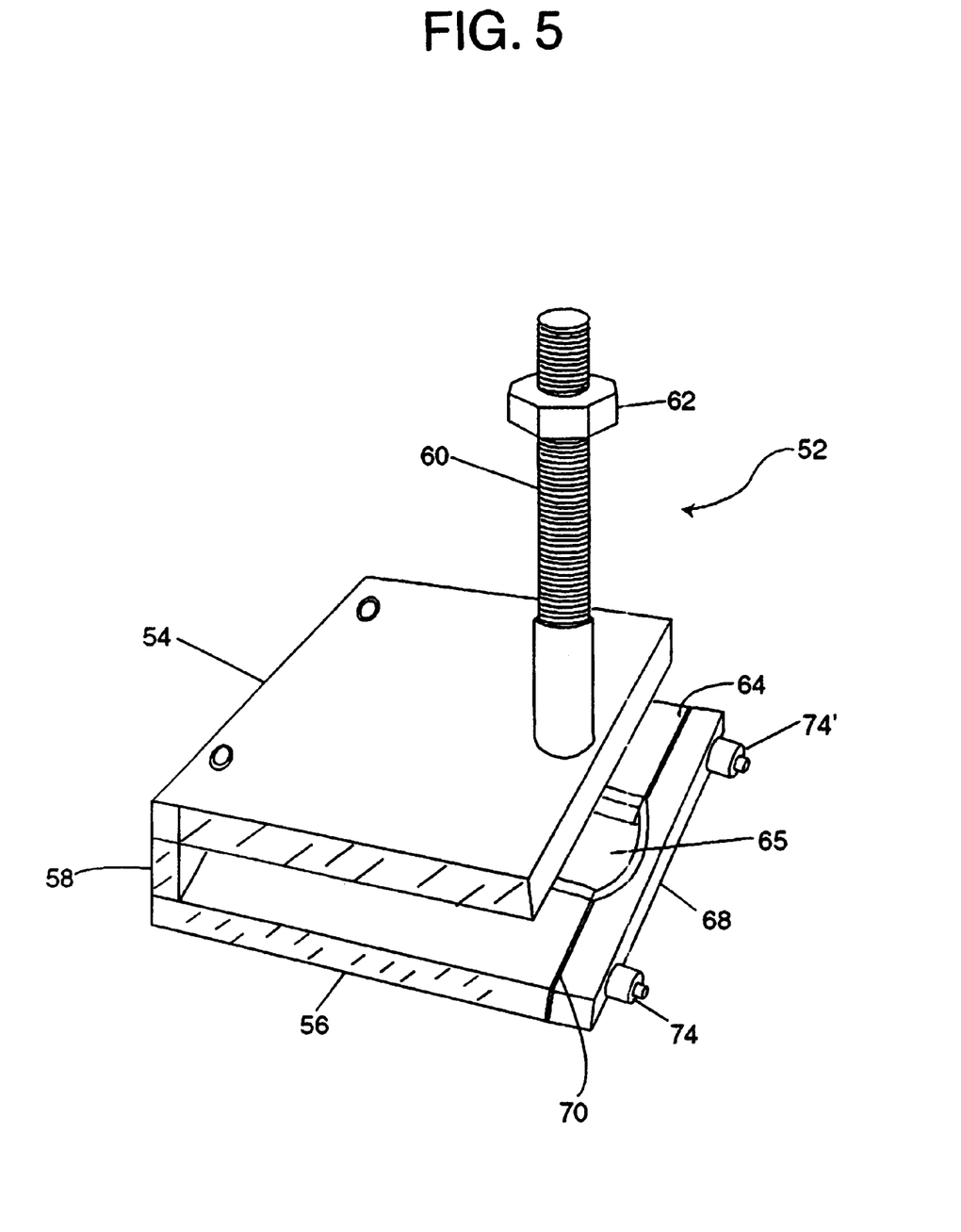
FIG. 5 shows in perspective view the tip removal member with a locking bar, a threaded rod and a locking nut constituting a part of the present invention.
Figures 6, 9, 10:
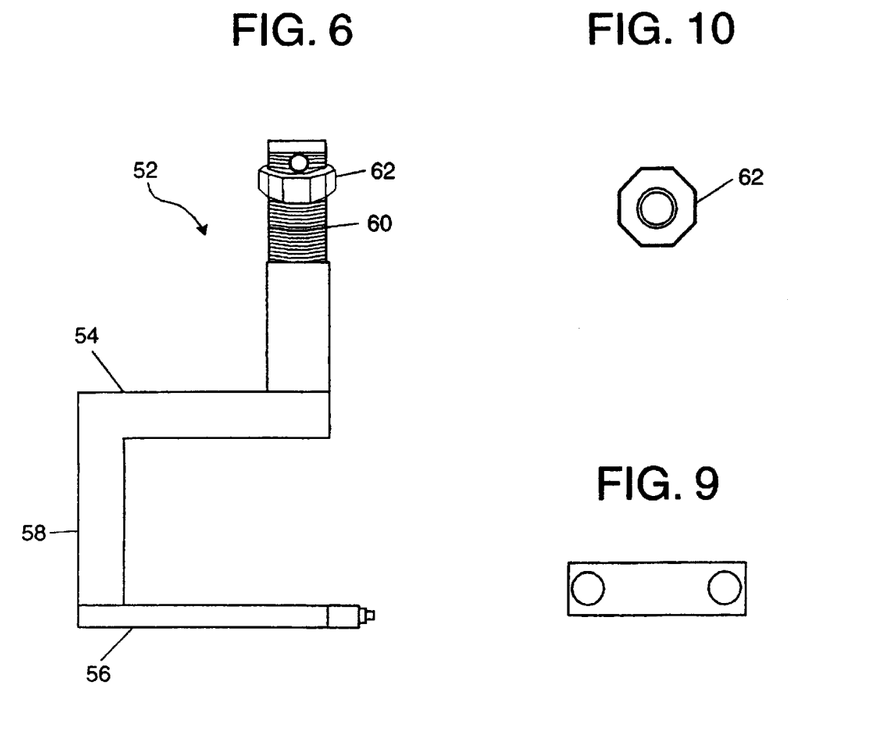
FIG. 6 is a side elevational view of the tip removal member shown in FIG. 5.
FIG. 9 is a front elevational view of the locking bar.
FIG. 10 is a top plan view of the locking nut.

Referring to FIGS. 2, 5, 6, 7, 8, 9 and 10, the apparatus of the present invention further comprises a closure removal means generally designated by the numeral 52 Closure removal means, as best seen in FIG. 5, comprises a horizontal top panel 54, a horizontal bottom panel 56 paralleled to each other, a vertical back panel 58 which holds the top and bottom panels together, and a threaded rod 60 extending distally from the horizontal tip panel.

Threaded rod 60 is inserted into rod receiving member 50 ad secured thereinto with locking nut 62.

Figure 7:
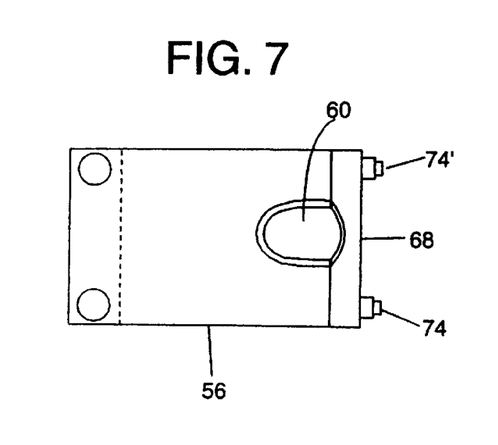
FIG. 7 is a bottom plan view of the locking bar in closed position.
Figure 8:
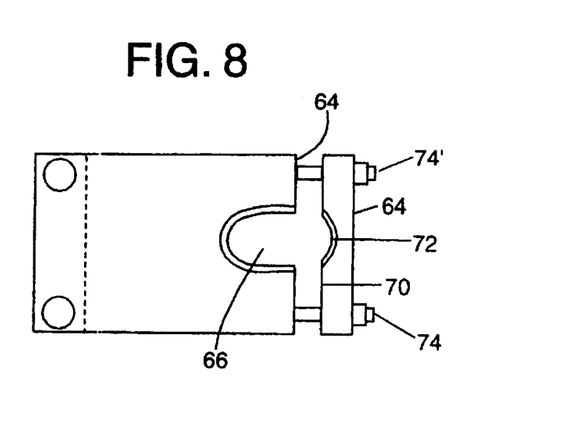
FIG. 8 is a bottom plan view of the locking bar in open position.

Horizontal bottom panel 56 has an edge 64 opposite and spaced from back panel 58 and comprises a semi-circular recess or hollow space 66 in the center thereof to receive elastomeric closure 20. Locking bar 64 is of rectangular configuration and is horizontally attached to bottom plate 56 at its edge 64. Locking bar has an edge 66 facing edge 58 of bottom plate 56 and comprises a semi-circular recess 72 which together with the semi-circular recess 66 in bottom panel 56 enclose a generally circular or oval space that serve for holding elastomeric closure 20. Locking bar 68 is equipped with adjustable screws 74 and 74' to move locking bar 68 toward the edge 64 of bottom panel 56 in order to close elastomeric closure 20 when closure removal is desired. Locking bar in the open 20 position is shown in FIG. 8 while in the closed position it. is shown in FIG. 7.

It is to be noted that barrel mounting means 38 is made to accommodate various barrels of syringes and cartridges having a volume of from 5 ml to 500 ml. Accordingly, the outside diameter of the mounting plate 42 and clamp ring 44 is sized to accommodate barrels having various outside diameters.

The method of removing an elastomeric closure 20 from a barrel 10 of a cartridge or syringe comprises the steps of:

positioning and securing barrel 10 in barrel mounting means 38 by placing the barrel in clamp ring 44 and turning the barrel so that flange 22 is engaging slots 48 and 48';

lowering horizontal member 34 holding closure removal means 52 until elastomeric closure 20 is in semi-circular recess 66 of horizontal bottom panel 56, closing locking bar by adjustable screws 74 and 74' so that elastomeric closure 20 is tightly gripped in the circular or oval space 66 and 72;

moving movable member 34 toward the distal, top portion of housing 28 by electronic means to remove elastomeric closure 20 from barrel 10.

Upon removal of the elastomeric closure of the barrel the present invention provides an apparatus for measuring the breakaway and driving forces required to move the plunger from its initial stationary position toward the distal end of the barrel to expel the content of the barrel.

Figure 11:
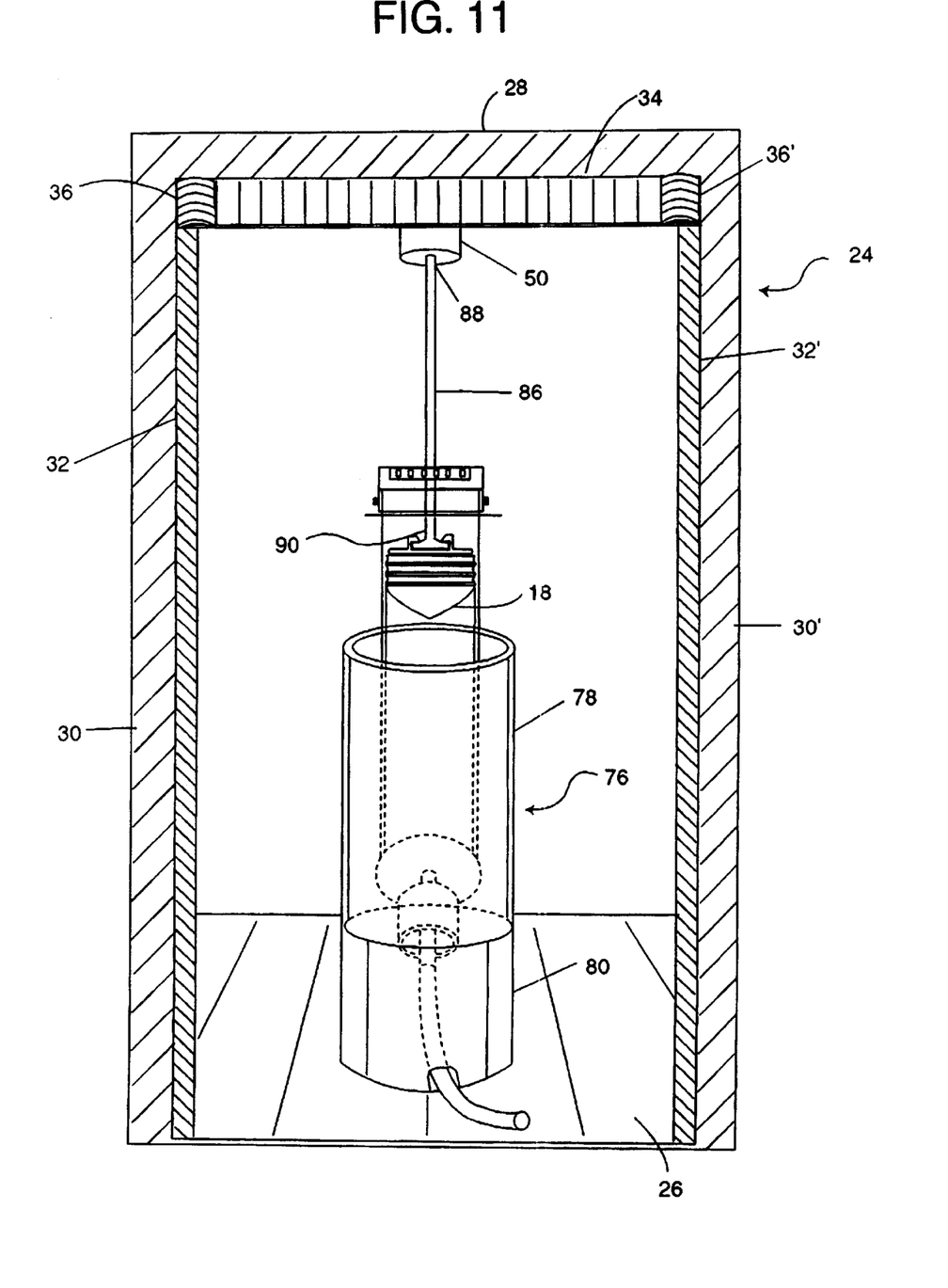
FIG. 11 shows in a perspective view the apparatus of the present invention for measuring the breakaway and running forces of a plunger in a cartridge barrel.
Figure 12:
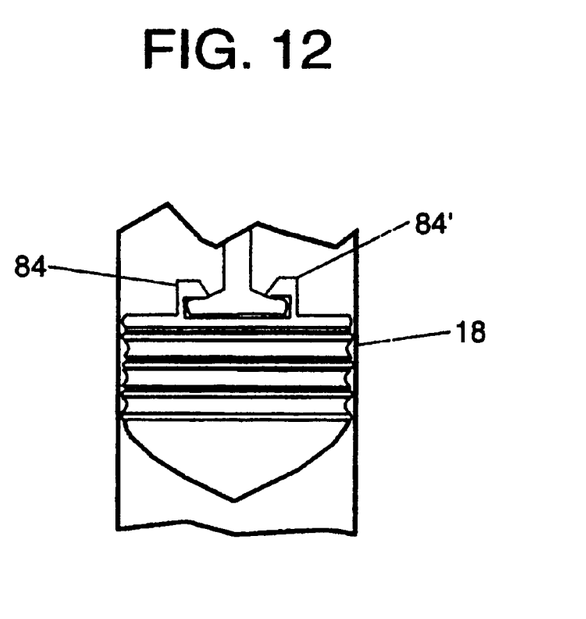
FIG. 12 shows a partial side elevational view of a cartridge barrel, plunger and plunger rod engaged with the plunger.
Figure 12A:
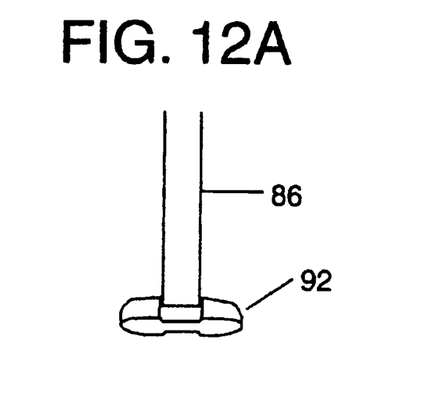
FIG. 12A shows a partial side elevational view of the plunger rod having a cross bar at the distal end thereof which engages the plunger.
Figure 12B:
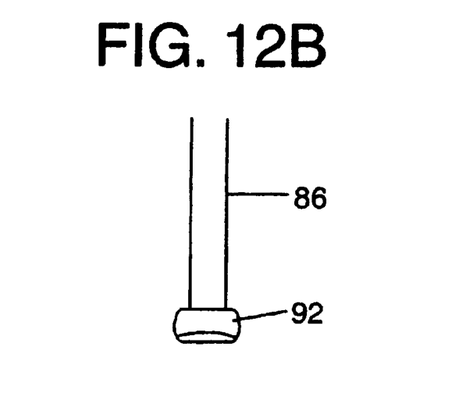
FIG. 12B shows a partial side elevational view of the plunger rod having a cross bar at the distal end thereof when the cross bar is turned 90°0 from its position shown in FIG. 12A.

Referring to FIG. 11, the apparatus includes:

a housing 24 of a generally rectangular box-shape configuration having a horizontal bottom portion 26 which serves as a platform, a horizontal top portion 28 and bottom side portions 30 and 30' connected to the top and bottom portions enclosing a rectangular space therebetween in which the remaining portions of the apparatus are located. Adjacent and parallel to vertical side portions 30 and 30' are male-threaded guidance rods 32 and 32' affixed to vertical side portions 30 and 30'. Horizontal member 34 extending to threaded guidance rods 32 and 32' are equipped at its end portions 36 and 36' with female threaded means for slideable vertical movement on the threaded guidance rods. Horizontal member 34 is designed to travel vertically between said horizontal top portion and said horizontal bottom portion. Electronic drive and control means (not shown) move the horizontal member vertically which control means can be equipped with electronic data output means expressing the force required to move the horizontal member and testing features removably attached to it. Such equipment is well known in the prior art and is available from Instron Corporation, MA, for example INSTRON Series 5500.

Figure 13:
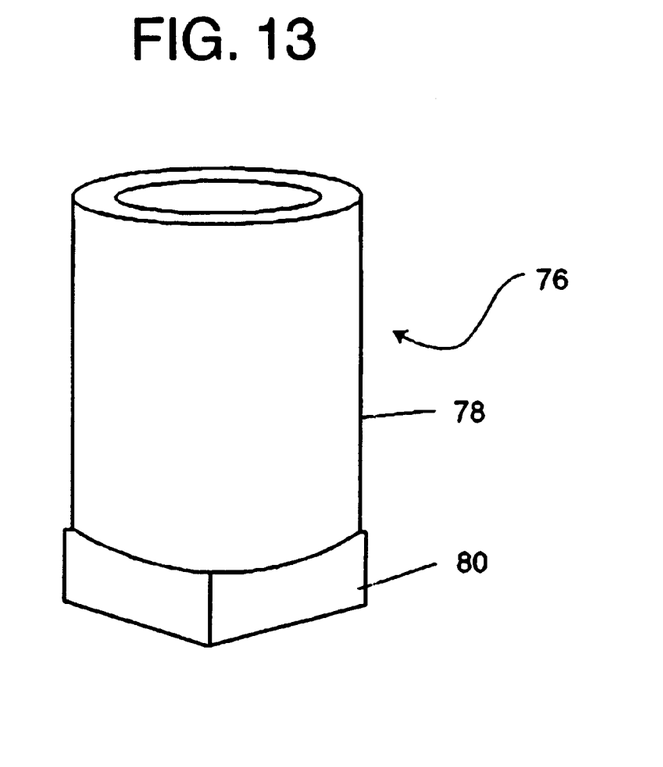
FIG. 13 shows in a perspective view the cylindrical mounting block constituting a part of the present invention shown in FIG. 11.

Placed on horizontal bottom portion 26 of the housing is a mounting block 76 made of a plastic material to receive and safely hold barrel 10. Mounting block is a thick walled holder for the barrel having a thickness of from about 0.5 to 30 mm or more, to insure safety of the person performing the testing if the barrel, being made of glass, shatters during the testing procedure. The mounting block is designed to hold at least a part, and preferably the whole length of the barrel and comprises:

a cylindrical top portion 78 and a generally rectangular shape bottom portion 80 as shown in FIGS. 11 and 13.

Figure 14:
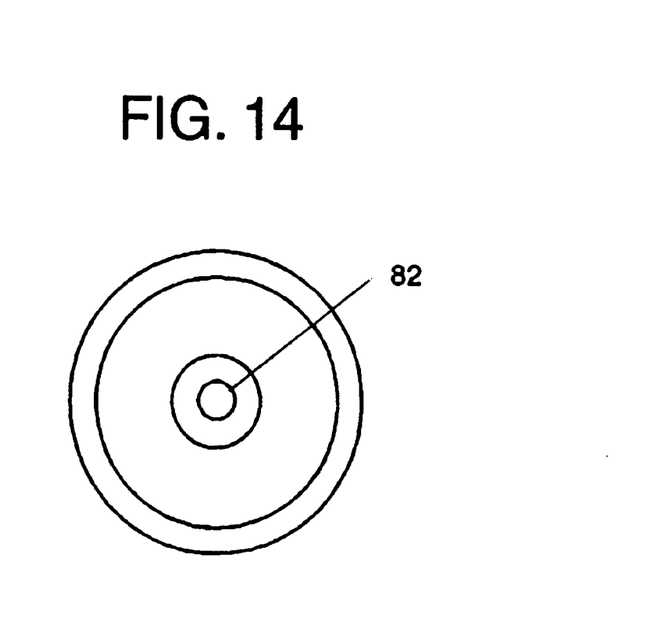
FIG. 14 shows a top plan view of the cylindrical mounting block.

Cylindrical top portion 78 is sized to receive barrels of various outside diameter sizes. Rectangular-shaped bottom portion 80 also comprises a cylindrical inside tapered toward the proximal end thereof terminating in a bore 82 as best seen in FIG. 14 to receive the tapered tip 15 at the proximal end 16 of barrel 10. This insures that the force exerted on the plunger, when measuring breakaway and driving forces, will not crush the tapered tip of the barrel.

The barrel is placed inside the mounting block in an upside-down position, i.e. the distal end of the barrel is placed in bore 82 of mounting block 76. Proximal end of barrel having plunger 18 equipped with coupling means 84 and 84' is connected to rod 86, which in turn is inserted and secured into rod receiving member 50. Rod 86 having distal end 88 and proximal end 90 is equipped at its proximal end with cross bar 92 which is of generally rectangular shape to engage coupling means 84 and 84'. Upon engagement horizontal member 34 is moved by electronic means toward bottom plate 26 forcing plunger 18 towards the distal end 14 of barrel 10. Electronic driving means (not shown) displays the breakaway and running forces of the plunger in the barrel.

The method of measuring the breakaway and running forces of a plunger contained in a pre-filled cartridge or syringe barrel comprises the steps of:

positioning barrel 10 in mounting block 76 by inserting the tapered tip 15 of the barrel from which the elastomeric closure was removed into the bore 82 of the mounting block;

releasably connecting the proximal end of the plunger 18 to the vertically movable member 34 by inserting cross bar 92 on proximal end 90 of rod 86 into coupling means 84 and 84' of plunger 18, and connecting distal end of rod 88 to rod receiving member 50;

moving plunger 18 from its stationary position in the proximal end 16 of barrel 10 toward distal end 14 of barrel by electronic drive means; and measuring the breakaway and running forces required to start moving the plunger and to continue moving the plunger in said barrel.

List of Reference Numerals

Cartridge or syringe barrel 10
Inner surface of barrel 12
Cylindrical chamber 13
Distal end of barrel 14
Tapered tip of barrel 15
Proximal end of barrel 16
Plunger 18
Elastomeric closure 20
Flange on proximal end of barrel 22
Housing 24
Horizontal bottom portion of housing 26
Horizontal top portion of housing 28
Vertical side portions of housing 30 and 30'
Male-threaded guidance rods 32 and 32'
Horizontal member 34
Female-threaded means at ends of horizontal member 36 and 36'
Barrel mounting means 38
Bolts for barrel mounting means 40
Mounting plate 42
Clamp ring 44
Bolts to affix clamp ring to mounting plate 46
Slots in clamp ring 48 and 48'
Rod receiving member 50
Closure removal means generally designated 52
Horizontal top panel 54
Horizontal bottom panel 56
Vertical back panel 58
Threaded rod 60
Locking nut 62
Edge of horizontal bottom panel 64
Semi-circular recess in bottom panel 66
Locking bar 68
Edge of locking bar 70
Semi-circular recess in locking bar 72
Adjustable screws on locking bar 74 and 74'
Mounting block 76
Cylindrical top portion of mounting block 78
Rectangular shape bottom portion of mounting block 80
Bore in rectangular shape mounting block 82
Coupling means on plunger 84 and 84'
Rod 86
Distal end of rod 88
Proximal end of rod 90
Cross bar on rod 92

The present invention has been described in detail with reference to preferred embodiments thereof, however, it will be understood that variations and modifications can be effected within the spirit and scope of the invention.

What is claimed is:

1. An apparatus for measuring breakaway and running forces required to move a plunger in a cartridge barrel said cartridge barrel having proximal end stoppered by a slidable plunger therein, and an open tapered distal end wherein said cartridge barrel is pre-filled with an injectable solution, the apparatus comprising:

a housing of generally rectangular configuration having a horizontal bottom portion, a horizontal top portion and two vertical side portions connected to and being integral with said horizontal top portion and said horizontal bottom portion enclosing a space therebetween, said housing being open at its front and back portions thereof;

threaded guidance rods affixed to said vertical side portions extending from said horizontal bottom portion to said horizontal top portion;

an electronically movable horizontal member extending to said vertical side portions engaging said vertical side portions and traveling vertically between said horizontal top portion and said horizontal bottom portion;

electronic drive and control means for moving said movable member and for measuring a force required to move said plunger in said barrel;

a barrel mounting block positioned on said horizontal bottom portion of said housing comprising a cylindrical top portion and a generally rectangular shape bottom portion, said barrel mounting block having a cylindrical inside cavity therein tapered toward the bottom portion and terminating in a bore to receive a cartridge barrel in an upside down position;

a rod having a distal end and a proximal end attached by its distal end to said movable horizontal member, and releasably attached by its proximal end to a plunger;

said electronic drive and control means designed to move said plunger from its stationary position toward the distal end of said cartridge barrel for measuring the breakaway and running forces required to move said plunger in said cartridge barrel.

2. A method of measuring breakaway and running forces required to move a plunger in a cartridge barrel said cartridge barrel having a proximal end stoppered by a slidable plunger therein, and an open tapered distal end wherein said cartridge barrel is pre-filled with an injectable solution, the method comprising:

(a) providing a housing of generally rectangular configuration having a horizontal bottom portion, a horizontal top portion and two vertical side portions connected to and being integral with said horizontal top portion and said horizontal bottom portion enclosing a space therebetween, said housing being open at its front and back portions thereof;

threaded guidance rods affixed to said vertical side portions extending from said horizontal bottom portion to said horizontal top portion;

an electronically movable horizontal member extending to said vertical side portions engaging said vertical side portions and traveling vertically between said horizontal top portion and said horizontal bottom portion;

electronic drive and control means for moving said movable member and for measuring a force required to move said plunger in said barrel;

a barrel mounting block positioned on said horizontal bottom portion of said housing comprising a cylindrical top portion and a generally rectangular shape bottom portion, said barrel mounting block having a cylindrical inside cavity therein tapered toward the bottom portion and terminating in a bore to receive a cartridge barrel in an upside down position;

a rod having a distal end and a proximal end attached by its distal end to said movable horizontal member, and releasably attached by its proximal end to a plunger;

said electronic drive and control means designed to move the plunger from it stationary position toward the distal end of the cartridge barrel and is capable of measuring the breakaway and running forces required to move said plunger in said cartridge barrel;

(b) placing the pre-filed cartridge barrel upside down into said barrel mounting block;

(c) activating said electronic drive and control means to move said plunger from its stationary position toward the distal end of the cartridge barrel; and (d) measuring by electronic means the breakaway and running forces required to move the plunger in said cartridge barrel.

\* \* \* \* \*